(12) United States Patent
Pineda et al.

(10) Patent No.: US 7,460,903 B2
(45) Date of Patent: Dec. 2, 2008

(54) METHOD AND SYSTEM FOR A REAL TIME ADAPTIVE SYSTEM FOR EFFECTING CHANGES IN COGNITIVE-EMOTIVE PROFILES

(76) Inventors: Jaime A. Pineda, 12682 Torrey Bluff Dr., #239, San Diego, CA (US) 92130; Brendan Z. Allison, 20 Marietta St., Apt. 15B, Atlanta, GA (US) 30303

( * ) Notice: Subject to any disclaimer, the term of this patent is extended or adjusted under 35 U.S.C. 154(b) by 973 days.

(21) Appl. No.: 10/661,658

(22) Filed: Sep. 12, 2003

(65) Prior Publication Data
US 2004/0138578 A1 Jul. 15, 2004

Related U.S. Application Data

(63) Continuation-in-part of application No. 10/376,676, filed on Feb. 26, 2003, now abandoned.

(60) Provisional application No. 60/398,508, filed on Jul. 25, 2002.

(51) Int. Cl.
*A61B 5/04* (2006.01)
(52) U.S. Cl. ...................... 600/544; 600/545
(58) Field of Classification Search .............. 600/9, 600/12–15, 544–545
See application file for complete search history.

(56) References Cited

U.S. PATENT DOCUMENTS

| | | | | |
|---|---|---|---|---|
| 4,883,067 A * | 11/1989 | Knispel et al. | .............. | 600/545 |
| 4,940,453 A * | 7/1990 | Cadwell | .............. | 600/13 |
| 4,949,726 A * | 8/1990 | Hartzell et al. | .............. | 600/544 |
| 5,392,788 A * | 2/1995 | Hudspeth | .............. | 600/544 |
| 5,465,729 A * | 11/1995 | Bittman et al. | .............. | 600/545 |
| 6,021,346 A * | 2/2000 | Ryu et al. | .............. | 600/544 |
| 6,132,361 A * | 10/2000 | Epstein et al. | .............. | 600/13 |
| 6,292,688 B1 * | 9/2001 | Patton | .............. | 600/544 |
| 6,349,231 B1 * | 2/2002 | Musha | .............. | 600/544 |
| 6,652,470 B2 * | 11/2003 | Patton et al. | .............. | 600/549 |
| 6,983,184 B2 * | 1/2006 | Price | .............. | 600/544 |
| 2002/0077534 A1 * | 6/2002 | DuRousseau | .............. | 600/300 |
| 2005/0124848 A1 * | 6/2005 | Holzner | .............. | 600/9 |

* cited by examiner

*Primary Examiner*—Robert L. Nasser, Jr.
*Assistant Examiner*—Karen E Toth
(74) *Attorney, Agent, or Firm*—Procopio, Cory, Hargreaves & Savitch LLP; Kam W. Li, Esq.; Lisel M. Ferguson, Esq.

(57) ABSTRACT

A means and method for inducing a temporary physiological state-of-mind to effect persistent changes to the cognitive-emotive profile of an individual, which is adaptable for neurofeedback and "mental-state" therapeutic and non-therapeutic interventions. The system comprises an EEG Recording Module (ERM), a Neurodynamics Assessment Module ("NAM"), and a Transcranial Magnetic Stimulation module ("TMS") for acquiring and manipulating bioelectrical and/or EEG data, defining a cognitive-emotive profile, and mapping the cognitive-emotive profile to selectively control transcranial magnetic stimulation to drive therapeutic and non-therapeutic stimulus interventions. A bi-directional feedback feature is provided to further enhance the performance of the system to effect prolonged changes.

34 Claims, 5 Drawing Sheets

METHOD AND SYSTEM FOR A REAL TIME ADAPTIVE SYSTEM FOR EFFECTING CHANGES IN COGNITIVE-EMOTIVE PROFILES

CROSS REFERENCE TO RELATED APPLICATION

This application claims priority to provisional patent application Ser. No. 60/398,508 filed on Jul. 25, 2002, and is a continuation-in-part of U.S. patent application Ser. No. 10/376,676, filed Feb. 26, 2003, now abandoned.

FIELD OF THE INVENTION

The present invention relates to a system and methods for adaptive intervention to effect changes in the cognitive-emotive profile of an individual. In particular, this invention involves the use of brain stimulation techniques using magnetic fields and characterization of bioelectric activity for producing real-time, adaptive changes in cognitive-emotive profiles.

BACKGROUND OF THE INVENTION

Many areas of the brain are involved in planning, organizing, problem solving, emotional self-regulation and other "higher cognitive functions" that closely relate to an individual's cognitive-emotive profile. More specifically, these include mechanisms to plan actions toward a goal, use information flexibly, recognize the consequences of behavior, and make inferences based on limited information. These mechanisms impact the management of sub-goal structures, such as the activations and switching between mental representations and procedures, assembling cognitive operations, multi-tasking, attentional and mnemonic control, the imposition of biases on the selection of task relevant information, evaluatory processes detecting potential for error and response conflict, and suppression of automatic and inappropriate behaviors (i.e., impulse control). Furthermore, cortical circuits connect extensively and work intimately with lower-level limbic circuits, (including anterior cingulate cortex, amygdala and hippocampus) to add emotional valence to these behaviors. Overall, these circuits are believed to mediate functions that determine an individual's cognitive-emotive profile.

Primary deficits occasioned by organic or traumatic events can cause functional disruption to cognitive-emotive circuits in areas of the brain that are then reflected in loss of control, initiation, cessation, control of action, cognitive estimation, cognitive flexibility, deficits in the response to novelty, goal-directed behaviors and the ability to sequence. Many of these deficits are reflected in the symptoms of specific malfunctions such as chronic fatigue, pain, tinnitus, epilepsy, depression, sleep disorders, and addiction, among others.

In co-pending U.S. patent application Ser. No. 10/376,676, of inventorship common to the present application, which is incorporated hereto as though set forth in full, it is shown that brain bioelectric signals can provide a window into the complex dynamics of brain activity related to sensation, motor, and cognitive-emotive behavior. As further discussed in application Ser. No. 10/376,676, various bioelectrical and more particularly the electroencephalogram (EEG) signal can be analyzed to define a cognitive-emotive profile of an individual. Because of recent improvements in biological sensor technology, signal processing methodology, pattern recognition techniques, and high-speed computational algorithms, the development and use of techniques to obtain and process biological signals in real time have improved considerably, thus facilitating the analysis of such bioelectrical data.

However, current technologies do not work by controlling levels of external therapy, lack rapid bi-directional control, and are quite insensitive to the user's cognitive-emotive profile. While they primarily deal with reducing or eliminating illness, they do not focus on improving individual wellness. Additionally, existing technologies are psychologically demanding and require long periods of time to effect the desired therapeutic changes.

What is needed is a means and a method to induce a temporary state-of-mind using low-level, pulsed magnetic fields to effect persistent changes in the cognitive-emotive profile of the individual. Such a system should rapidly recognize the functional significance of the mental and brain function. Moreover, such a system could be used, though not limited, to enhance cognition, enhance wellness, improve quality of medical care, reduce the time to therapeutic effectiveness, improve the quantity and quality of interrogations, and diminish the intervention time necessary to ameliorate specific disorders such as chronic fatigue, pain, tinnitus, depression, sleep disorders, and addiction.

SUMMARY OF THE INVENTION

The present invention provides a method and a real time adaptive system for effecting changes in the cognitive-emotive profiles of any individual. The invention integrates a combinatorial recording approach with a combinatorial stimulation approach, which enables real time, adaptive changes. The system comprises a portable headset that includes a matrix of electroencephalogram (EEG) recording sensors, a neurodynamics assessment box, a plug-and-play TMS device and a set of software tools that allow for real-time, bi-directional feedback of EEG signals. It also includes the controls for the array of magnetic field coils that produce temporary changes in a physiological state-of-mind leading to persistent change in an individual's cognitive-emotive profile. The headset device captures bioelectric signals, as well as manages the low-level stimulation. Through activation-deactivation of targeted brain areas via TMS pulses, specific brain and mental states can be induced in which individuals experience cognitive-emotive changes, such as improvement in memory functions or a reduction/elimination of symptoms of an illness. Real time assessment of bioelectric indices is used to compute a multi-dimensional "state-of-mind" of the individual that reflects the assessment of current sensorimotor ("sense awareness") and psychological ("mental state awareness") states and their boundary conditions. This assessment can then be used to provide direct feedback to the user or to adjust the duration, timing, and pulsatile nature of the TMS coils at one or multiple positions on the head.

The system is real-time and adaptive to the changing state-of-mind of the individual. Hence, a course of treatment could involve an individual learning through a process of instrumental conditioning how to adjust the necessary level of stimulation and gradually decreasing or modifying such stimulation over time. The outcome would be a change in the individual's cognitive-emotive profile. The present invention can be used alone or in combination with other interventions to produce these desired changes.

DETAILED DESCRIPTION

The present invention comprises a means and method for inducing a temporary physiological state-of-mind to effect persistent changes to the cognitive-emotive profile of an individual. Capable of rapidly recognizing the functional significance of the mental and brain function, the invention represents a unique approach to neurofeedback and "mental-state" therapy. The invention makes possible sensitive management of types and levels of therapeutic and non-therapeutic interventions. The sense- and mental state-awareness responses, integrated into a two-way (i.e., bi-directional) feedback system using a dynamic interface with intelligently controlled thresholds, comprise a novel adaptive NeuroIntervention System™ (NIS). The invention takes into account details of multi-variate and nonlinear dynamics and database templates to more accurately compute the user's "state-of-mind." It then utilizes this "state-of-mind" to drive therapeutic and non-therapeutic stimulus intervention. By way of a "combinatorial TMS stimulation sequence" approach, the present invention creates a fine-tuned and well-controlled process. The significance of this interactivity is a prolonged change in the individual's cognitive-emotive profile.

Figure 1:
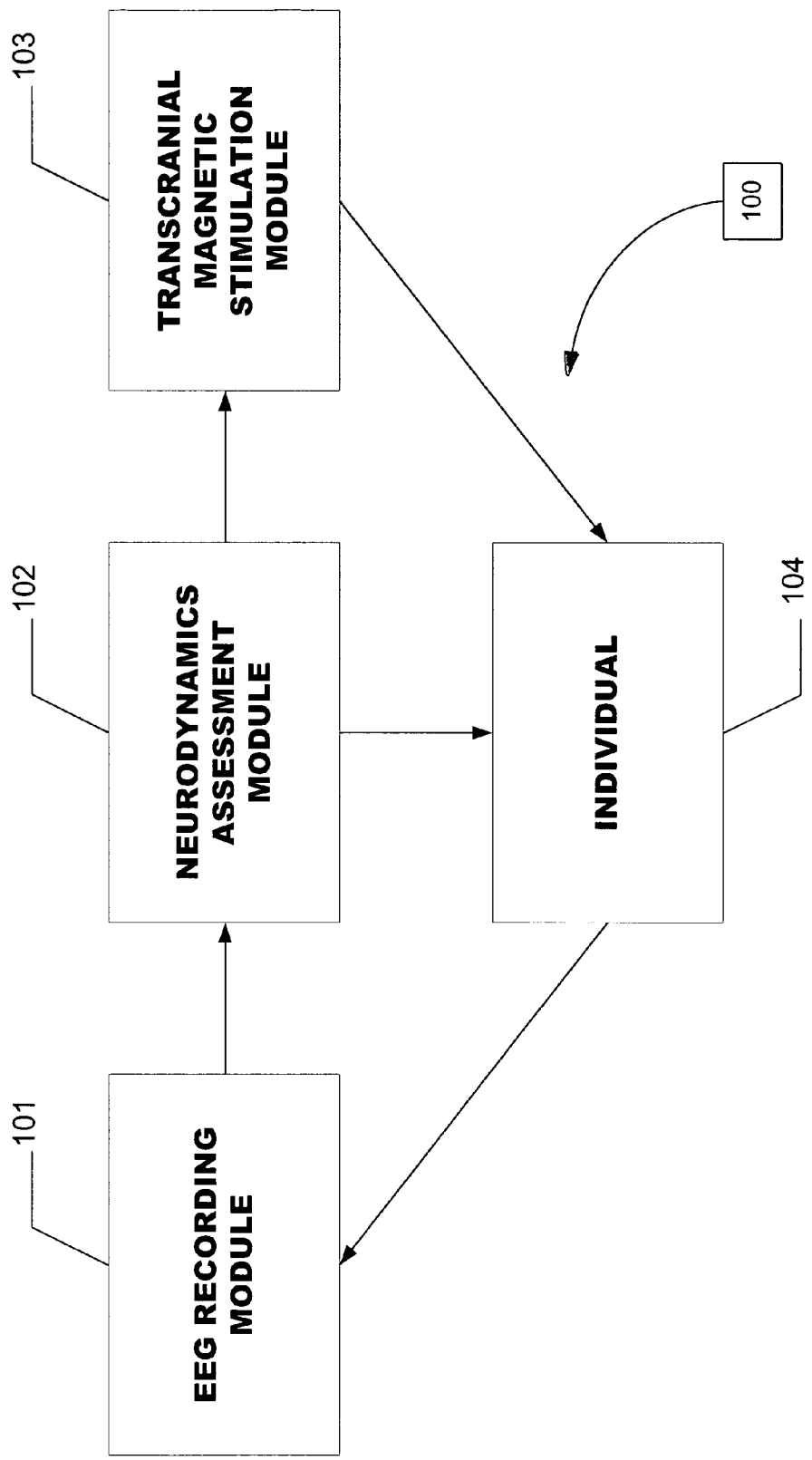
FIG. 1 is a block diagram depicting the various components and modules of the system for effecting changes in cognitive-emotive profiles of the present invention.

FIG. 1 is a block diagram representing the major components of the real time adaptive system to effect changes in the cognitive profiles of an individual 104. This system 100 comprises an EEG Recording Module (ERM) 101, a Neurodynamics Assessment Module ("NAM") 102, and a Transcranial Magnetic Stimulation module ("TMS") 103.

The ERM 101 provides a means for acquiring the bioelectric signals of the individual 104. It can be incorporated as part of a headset that also contains pluggable TMS coils. The headset consists of a high precision, low interference cap where EEG sensors are suitably positioned in proximity of strategically located site on the scalp such as the frontal parts of the brain to detect bioelectric signals. The EEG sensors may be embedded in commercially available conventional electrode caps, headbands, nets, virtual reality (VR) helmets, or other means placed on the head of the user. The sensors use wires and/or wireless means to convey information to the recording microprocessor. Additionally, the ERM 101 incorporates data-acquisition circuitry with high-bandwidth communications, which support free motion and continuous use, during self-controlled and guided-mode interventions and monitoring when the individual is alone. The ERM 101 utilizes electrodes optimized to record the maximal signal with the fewest number of recording biological sites of the individual's body, which is easy to put on and operate. It also includes circuitry that ensures excellent signal-to-noise and relatively noise- and artifact-free EEG signals.

Using the ERM 101, the EEG of the individual 101 is detected and digitized by an analog to digital board at a sampling rate that varies with functionality. The EEG sampling circuitry is gated to attenuate the effects of the nearby magnetic field pulses generated by the TMS stimulator(s).

The bioelectric signal, and/or derived signatures, is transmitted to a remote receiver that is connected to a portable microprocessor. Communication between components of the system and other external modules is bi-directional and options for its implementations make it network- and internet-ready.

The NAM 102 assesses the multi-dimensional, non-linear combination of sense- and mental state-awareness information from the bioelectric signals and provides a real-time snapshot of the individual's state-of-mind. The NAM 102 is integrated into an assessment regime that involves simultaneous measurements of multiple components of the brain signals to track stimulus depth, effectiveness and real-time cognitive, emotional, and behavioral responses relevant to the assessment regime.

The NAM 102 incorporates a portable data capture and analysis system with real-time monitoring capabilities supported by a suite of post-processing software modules for neurological, psychophysical, and psychological assessments. The NAM 102 acquires multiple brain signals from individuals using real-time analog-to-digital conversion and analysis of signals via the ERM 101 headset and incorporates the use of a dedicated microprocessor-based scientific software, which resides in the microprocessor computer for computerized analysis. The signals are converted into a digital stream and supported by the microprocessor-based software and database processing capabilities. The NAM 102 compares the current physiological state ("state-of-mind") to a set of templates or indices stored in normative databases to extract a temporary, multi-dimensional "cognitive-emotive profile," which reflects an accurate state of mind of the user, as discussed in more detail in co-pending application Ser. No. 10/376,676. This profile contains the individual, integrated electrophysiological indices and their associated boundary conditions and may be updated as necessary to be customized for individual users. The templates or indices are derived as a collection of the state-of-mind profiles from a plurality of individuals, which are manifested as the anticipated norm or baseline value. If the measured value of the individual profile is beyond this baseline value, intervention would be considered.

Figure 2:
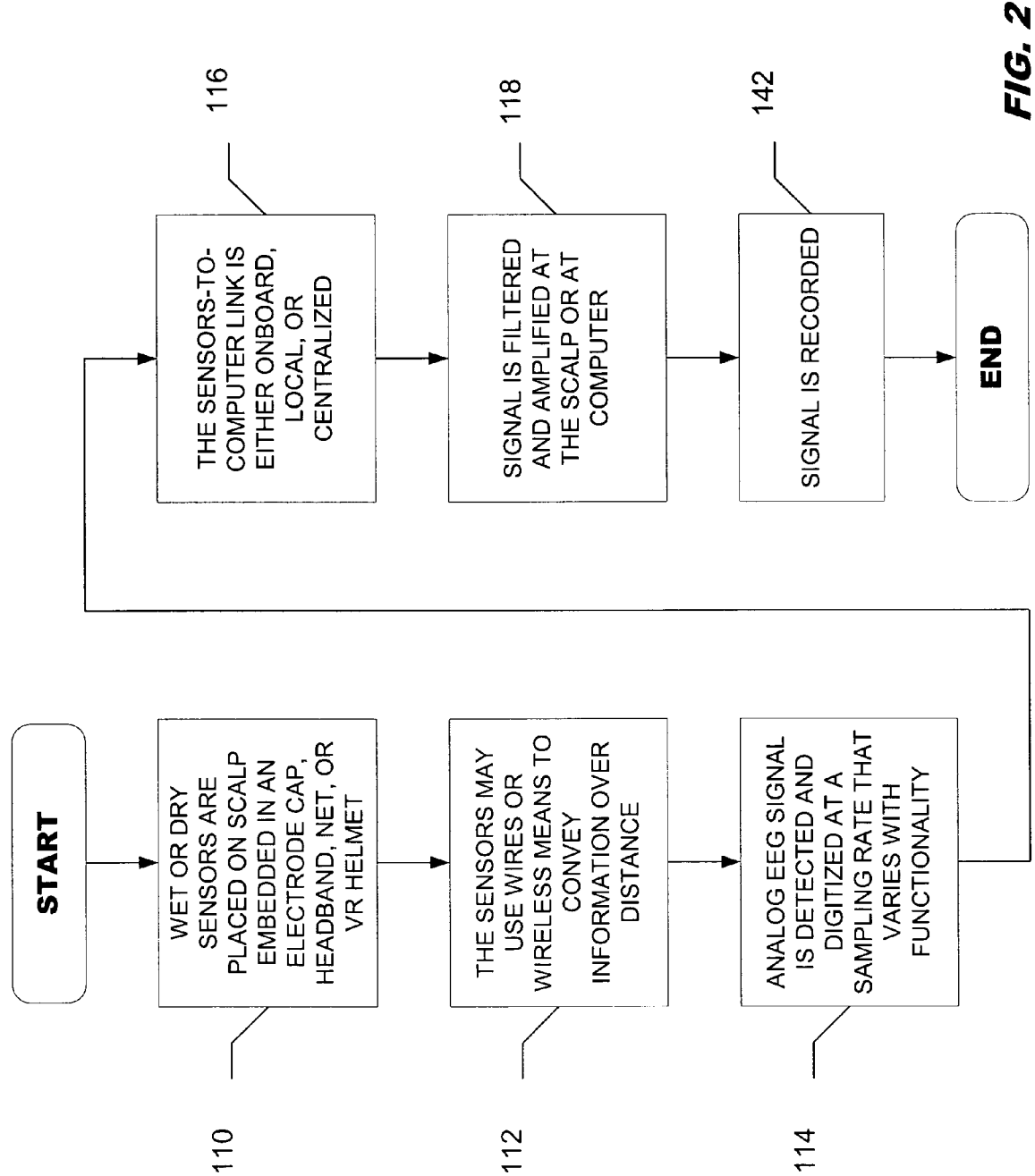
FIG. 2 shows the diagrammatic sequence of steps involved in the recording and stimulation stage.

The NAM 102 also includes digital filtering, signal averaging, real-time power spectrum analysis, and calculation of the ongoing power in different frequency bands. It provides data collection, real time analysis, and delivering of output based on the result of the analysis. FIG. 2 is a flow diagram of a method for brain signal acquisition of the present invention. In step 401, wet or dry sensors may be embedded in commercially available conventional electrode caps, headbands, nets, virtual reality (VR) helmets, or other means placed on the head of the individual 104. In step 402, the sensors use wires and/or wireless means to convey information to the recording microprocessor. In step 403, an EEG signals are detected and digitized by an analog to digital board at a sampling rate that varies with functionality. The sensors-to-microprocessor link, as indicated in step 404, can be onboard (i.e., both sensors and microprocessor are on the body); local (both sensors and microprocessor within a defined distance of each other); or centralized (both sensors and microprocessor at a very large distance from each other). The analog signal is filtered (bandpassed) and amplified (either at the scalp or remotely at the recording microprocessor), and digitized, as illustrated in step 405. In step 406, the signals are recorded.

Figure 3:
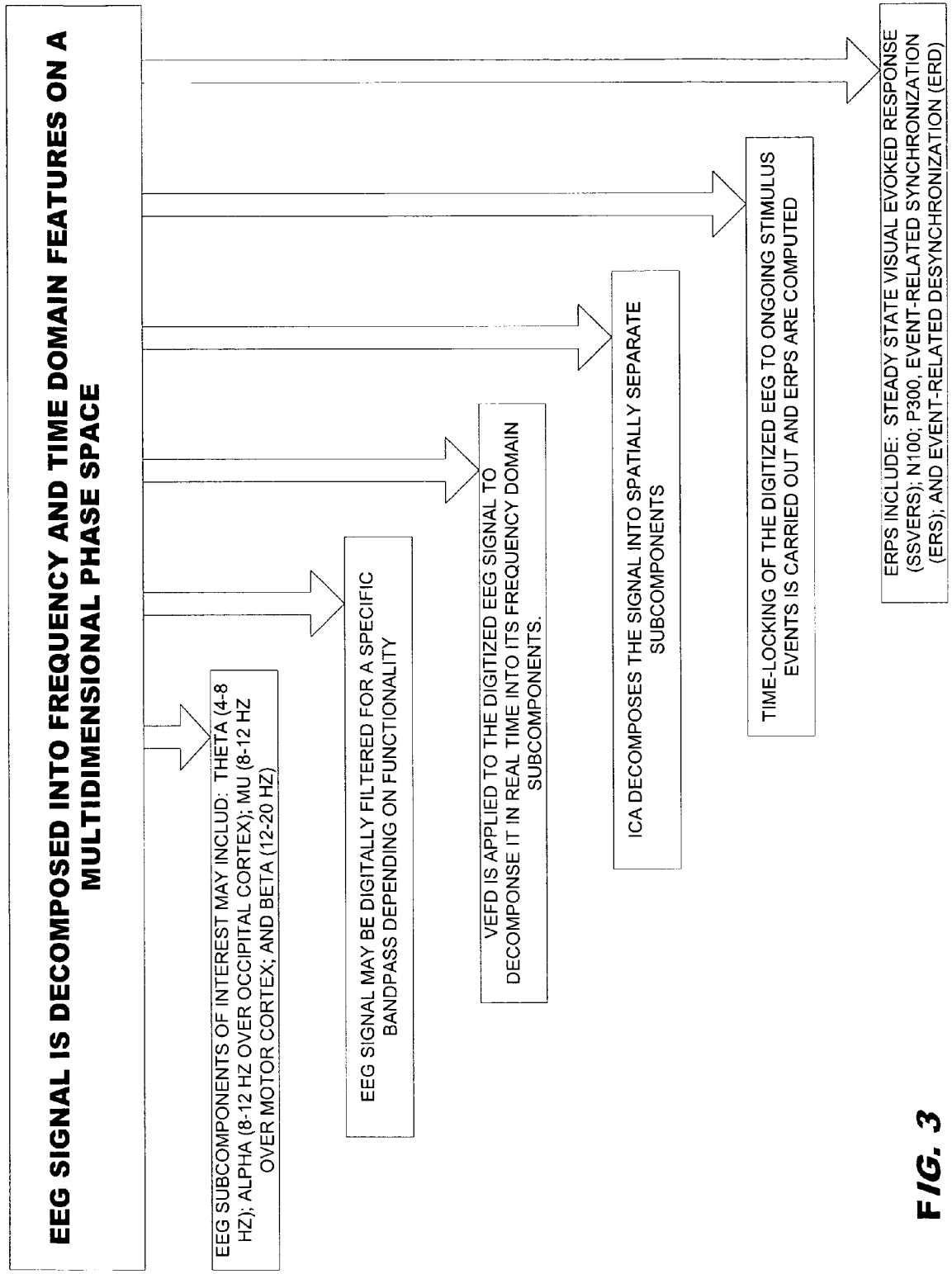
FIG. 3 depicts flow chart diagrammatic views of the decomposition and analysis of brain signals in accordance with the present invention.

As depicted in FIG. 3, the digitized EEG signal is decomposed into frequency and time domain features on a multidimensional phase space. Frequency and time domain subcomponents are analyzed using a variety of techniques, which could include Variable Epoch Frequency Decomposition (VEFD), Fast Fourier Transform, Event-Related Potentials (ERPs), Independent Component Analysis (ICA), Time-Frequency Expansion, and/or Feature Coherence Analysis. The EEG subcomponents of interest include EEG rhythms, such as mu (7-13 Hz over sensorimotor cortex), theta (4-8 Hz); alpha (8-12 Hz over occipital cortex); and beta (12-20 Hz). They can also include time-locked responses to external events, or event-related potentials, such as the traditional N1, P3, or the steady state visual evoked response (SSVER).

Figure 4:
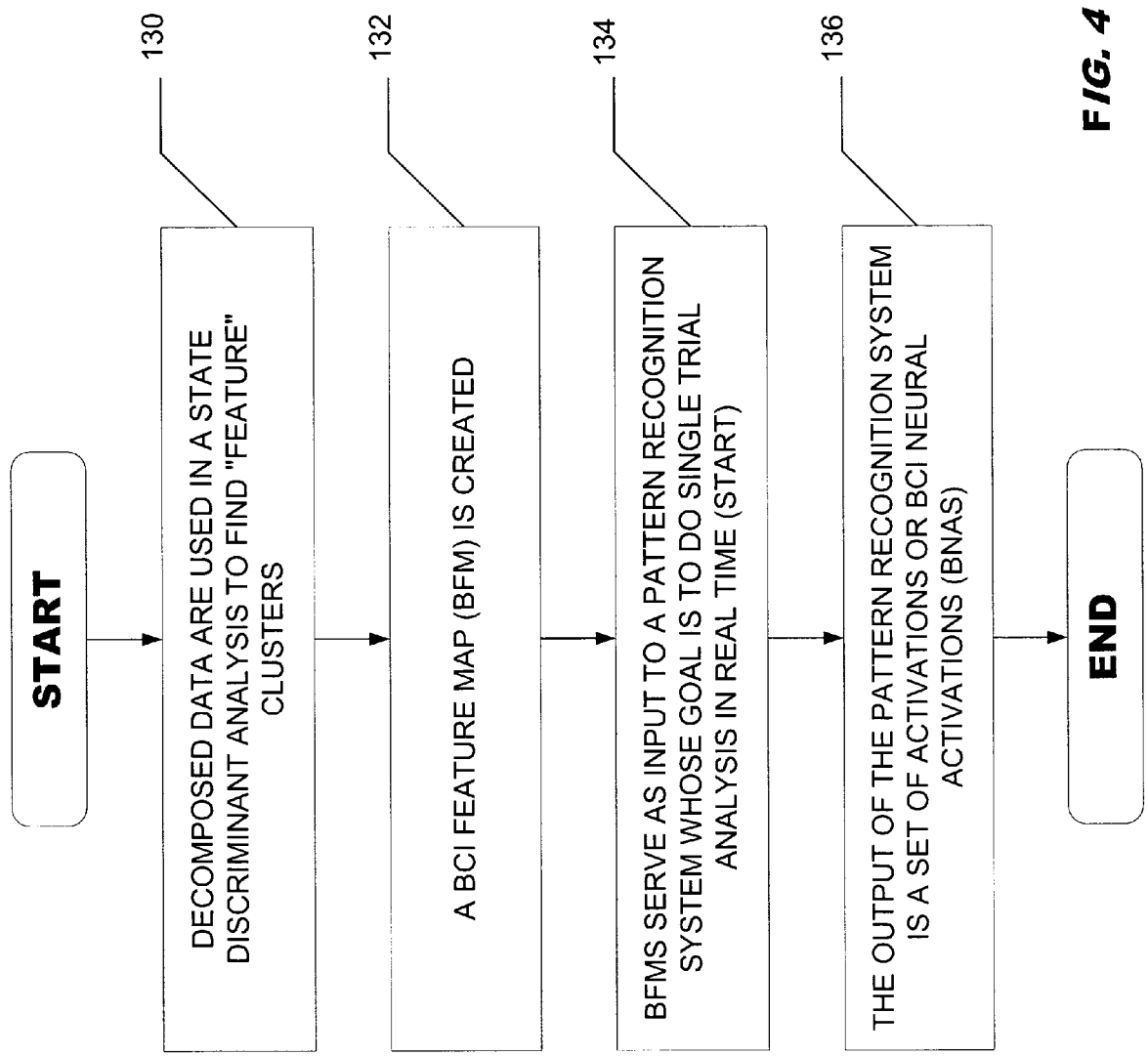
FIG. 4 depicts flow chart diagrammatic views of the learning and pattern recognition analysis of brain signals in accordance with the present invention.

As further shown in FIGS. 3 and 4, the EEG signal is digitally filtered for a specific bandpass depending on which of these signals is being used. In most applications, ICA decomposes the signal into spatially separable subcomponents in order to maximize the signal-to-noise response and allow for multiple control signals. The original data may be reconstituted using only ICA subcomponents that account for a large portion of the variance in the signals. This removes blinks and eye movement artifacts from the data. Using ICA to "clean" the data in real time increases signal-to-noise ratio, making the relevant signal easier and faster to detect by a pattern recognition system. Identification of multiple independent control signals in the EEG makes capturing a more realistic state of mind possible.

As shown in FIG. 4, step 601, decomposed EEG data are subjected to a state discriminant analysis to identify "feature" clusters that are most reliably different between different conditions. These feature clusters represent patterns of electrical activity that occur across the scalp and that are linked to specific thought patterns. They may be analyzed using waveform analysis, distribution function analysis, Fuzzy logic, discriminant optimization, and/or other approaches. The outcome in step 602 is the creation of a BCI Feature Map (BFM), which is represented as a set of parameters, components, functions, and criteria. In step 603, BFMs are constituted as input into a pattern recognition system, which may be expressed in the form of a neural network, genetic algorithm, Kohonen network, Fuzzy neural net, or Markov model. In step 604, the output of the pattern recognition system is a set of activations or BCI Neural Activations (BNAs). BNAs are derived from adaptive combinations of discriminant brainwave features in space, time, frequency, and phase that come together to maximize the contrast between conditions.

As referenced above, the present invention includes a TMS Module 103, which selectively stimulates specific cognitive-emotive brain circuits via magnetic stimulation. The TMS module allows for targeting of executive, decision-making and emotion-related functions of the brain by safe, low-level stimulation pulses of focused magnetic fields by an array of TMS coils. It also receives the feedback from the Neurodynamics Assessment module to the TMS device to adjust the combination of coils activated and the levels of stimulation to be used.

The TMS coils are integrated into a headset with the ERM, which can be worn by an individual. It includes circuitry that provides low-level pulsatile magnetic pulses to multiple yet specific areas of the brain. In the present invention, the TMS, applying a pulsed magnetic field with a high degree of specificity, is adapted to temporarily activate-deactivate brain cognitive-emotive circuits. It is noted that the effects of the TMS on the behavioral changes outlast the short time of actual stimulation and persist over longer time frames.

The TMS coil components are removable (i.e., plug-and-play) for ease of maintenance and for system weight reduction when only on-going monitoring and EEG feedback and mental intervention effects are required. The TMS module also includes the software to activate the TMS coil devices. The magnetic field is generated by the TMS in the form of microsecond-duration current pulses through coils placed in proximity of the scalp so that the field is focused in the cortex, passing through the skull unattenuated. When induced current pulses are delivered at regular intervals (in the range of <1 to 25 Hz) the electrical activity of brain cells below the coil become activated or deactivated, depending on the frequency of stimulation.

Figure 5:
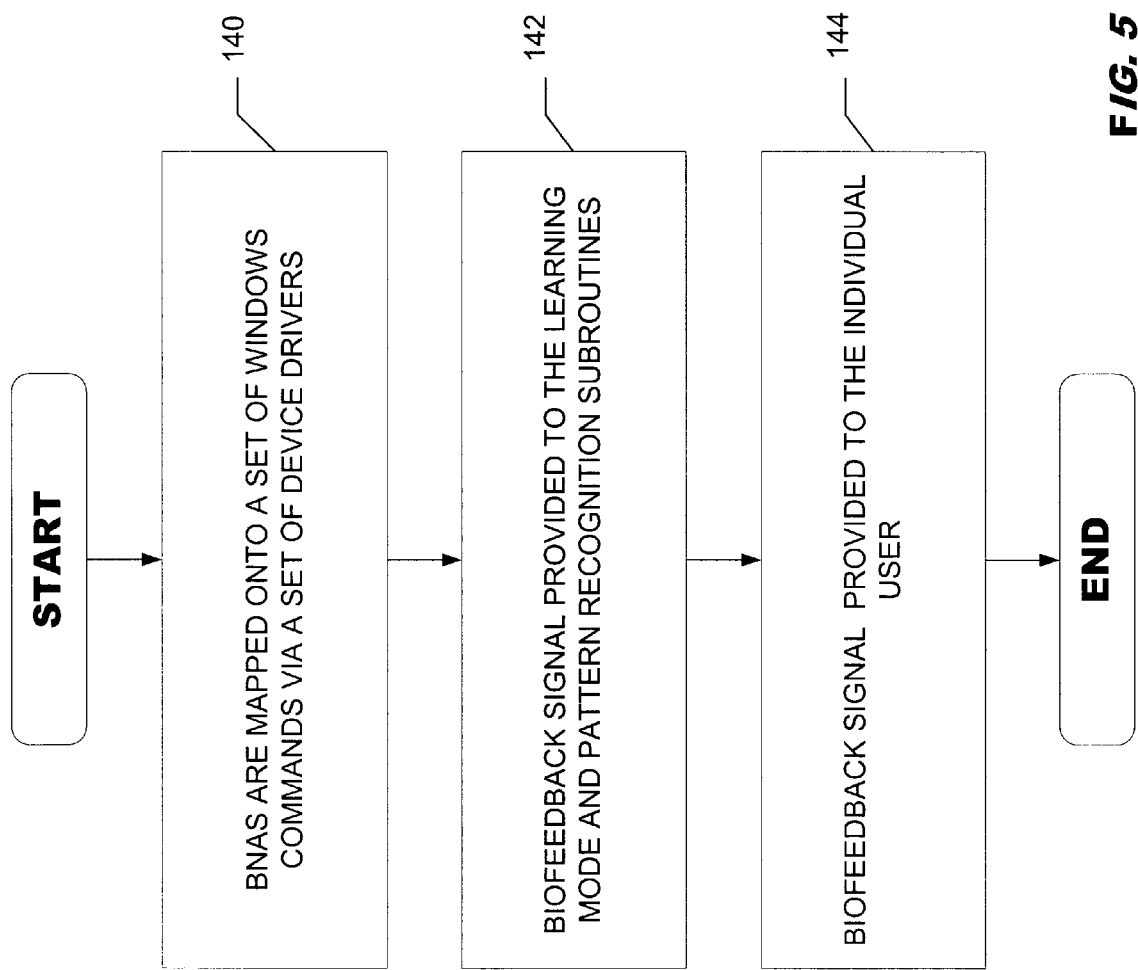
FIG. 5 depicts flow chart diagrammatic views of the computer interface and closed-loop feedback analysis of brain signals in accordance with the present invention.

The computer software system supporting the various components and modules includes a library of data analysis routines, from which bioelectric indices are obtained from the analysis of spontaneous, event-related, and steady state brain responses as well as other naturally occurring bioelectric activity. As depicted in FIG. 5, the indices are mapped to effect control of the TMS device, such as to adjust the combination and levels of stimulation on the individual coils. The software system is "sense-aware" and "mental-state-aware." These features are integrated into a part of the boundary conditions of the resulting cognitive-emotive profile. The present invention provides for software that allows for flexible mapping of this information. This sets up the mapping of accessible environmental events to the real-time system that controls the TMS stimulation and EEG recording procedures.

The sense- and mental state-awareness capabilities are activated when TMS stimuli are applied while individuals are engaged in performing an instrumented and well-characterized procedure or application. Examples of instrumented environments include interactive games, virtual reality, or other simulation environments, from which task-relevant parameters can be captured during performance.

For an interactive games environment that is appropriately instrumented for cognitive assessment, the event sequences and the individual subject's responses can be captured simultaneously for real-time steering of the TMS stimulation. Analysis may include examination of reaction times and appropriateness of subject responses. In the case of a virtual reality simulation that is appropriately instrumented for autonomic assessment, specific autonomic responses, such as heart rate, galvanic skin response, or temperature can be captured simultaneously to provide the sense-awareness.

The system software also provides a mapping capability with the ability to weigh variables and to apply them in appropriate calculations and to capture them in computer files for post-processing. A flexible embedded scripting language in the tool, and user memory in the main application, enables simple, limited conversions of data formats and conditional statement control that can run in real-time for appropriate system interfacing. The computational output is also used to provide visual feedback information to the subject and to adapt the data analysis/extraction algorithm to best match the incoming data (adaptive data extraction). As shown in FIG. 5, once a pattern of brain activity is identified by way of learning mode and pattern subroutines, step 701 dynamically (in real time) maps the BNAs onto a set of microprocessor-based system commands that reset the combination and levels of stimulation.

In step 702, a biofeedback signal is provided to the learning mode and pattern recognition subroutines. Finally, in step 703, a biofeedback signal is provided to the individual 104 for example by way of a video display. The dynamic mapping also allows advantages in several "open-loop" situations where the user does not necessarily need to detect and employ feedback to achieve robust assertion of a desired control. The system can be used in self-controlled mode, but also in guided-mode with cooperative and uncooperative individuals, such as in medical settings. In the self-controlled mode, the system increases the degrees of freedom that a person has over medical or non-medical treatments and gives an individual control over the level of stimulation required to change a "cognitive-emotive profile."

From the above, it is apparent that the present invention represents a unique, approach to neurofeedback and "mental-state" therapy. It takes into account details of multi-variate, nonlinear dynamics that more accurately reflect the user's "state-of-mind" and utilizes it to drive the therapeutic and non-therapeutic stimulus intervention. Thus, the present invention effectively integrates a "combinatorial TMS stimulation sequence" with a "combinatorial EEG recording sequence" to create a fine-tuned and well-controlled process. The significance of this interactivity is a prolonged change in the individual's cognitive-emotive profile.

This invention is deployable over diverse areas of human activity, including enhancing work performance, such as operator speed and accuracy, alternative learning techniques, military applications such as debriefings and interrogations, and rehabilitation for violent behavior and addictions of various types. Specific applications include, but are not limited to, monitoring brain disorders, ameliorating specific disorders (such as sleep disorders, mood disorders, OCD, attention-deficit and other attentional deficits), monitoring and inducing alertness and cognitive readiness in individuals to ensure they perform their jobs safely and adequately, having the ability to acquire information and to evaluate the validity, truth or falsity of such information, and aid in relaxation, motivation, or induction of other specific cognitive-emotive states desired by the user.

While the above description of the invention is directed to the present embodiments or examples of applications, various modifications and improvements can be made without departing from the spirit and scope of the invention.

What is claimed is:

1. A method of adaptive intervention for effecting persistent changes in the cognitive-emotive profile of an individual, comprising the steps of:
   selectively acquiring a plurality of bioelectric signals of the individual to determine current psychological state;
   comparing current psychological state to a set of templates or indices to extract a multi-dimensional cognitive-emotive profile based on the bioelectric signals;
   mapping the cognitive-emotive profile onto a set of commands;
   controllably delivering brain stimulation commands to the individual to drive therapeutic and non-therapeutic stimulus intervention; and
   effecting a prolonged change in the individual's cognitive-emotive profile which persist over long timeframes and outlast stimulation.

2. The method of claim 1, wherein the effected by transcranial magnetic stimulation (TMS) which results in behavioral changes.

3. The method of claim 2, wherein the TMS signal can be delivered at one or more sites of the individual's body simultaneously and the effects of the TMS on the behavioral changes outlast the short time of actual stimulation and persist over longer time frames.

4. The method of claim 1, wherein the bioelectric signal is an electroencephalogram (EEG) signal.

5. The method of claim 4, wherein the EEG signal is recorded from multiple recording sites from the scalp of the individual using a portable headset.

6. The method of claim 5, wherein the portable headset includes a matrix of EEG sensors and magnetic field coils oriented over specific areas of the brain of the individual.

7. The method of claim 4, further comprising the decomposition of the EEG signal into a plurality of signal subcomponents including:
   frequency domain subcomponents;
   time domain subcomponents; and/or spatial domain subcomponents.

8. The method of claim 7, wherein the frequency domain subcomponents are selected from a group consisting of a mu rhythm, a theta rhythm, an alpha rhythm, and a beta rhythm.

9. The method of claim 7, wherein the time domain subcomponents are selected from a group consisting of event-related potentials (ERPs) including N1, P3, and steady state visual evoked response (SSVER).

10. The method of claim 7, wherein the spatial domain subcomponents are selected from a group derived from special algorithmic transformation of the EEG signal.

11. The method of claim 7, wherein the frequency and time domain subcomponents are analyzed using one of a group of signal processing algorithms consisting of a variable epoch frequency decomposition (VEFD), a fast Fourier transform (FFT), and independent component analysis (ICA).

12. The method of claim 7, further comprising identifying and classifying feature clusters from the plurality of signal subcomponents.

13. The method of claim 12, further comprising creating a brain/computer interface feature map (BFM) from a feature cluster identified through one of a group of transformation algorithms consisting of:
   a discriminant optimization analysis;
   a wavelet analysis;
   a distribution function analysis; and
   fuzzy logic.

14. The method of claim 13, further comprising performing real-time pattern recognition on the BFM to produce a set of BCI neural activations (BNAs).

15. The method of claim 1, further comprising dynamically determining a cognitive-emotive profile of the user that reflects changing behavioral states.

16. The method of claim 15, wherein the cognitive-emotive profile is comprised of sensorimotor and psychological states and their boundary conditions.

17. A real time adaptive system for effecting changes in the cognitive-emotive profiles of an individual comprising:
   signal acquisition means for acquiring an electroencephalogram (EEG) signal from the individual;
   neurodynamics assessment means for analyzing the EEG signal to establish a cognitive-emotive profile;
   transcranial magnetic stimulation (TMS) means responsive to the cognitive-emotive profile to controllably deliver brain stimulation to the individual and interactive means for effecting persistent changes which outlast the stimulation to the cognitive emotive profile and result in improve memory function or reduction or elimination of symptoms of illness.

18. The real time adaptive system of claim 17, wherein the neurodynamics assessment means comprises means for decomposing the EEG signal into a plurality of signal subcomponents.

19. The real time adaptive system of claim 18, wherein the plurality of signal subcomponents comprises:
   frequency domain subcomponents;
   time domain subcomponents; and
   spatial domain subcomponents.

20. The real time adaptive system of claim 18, wherein the frequency domain subcomponents are selected from a group consisting of a mu rhythm, a theta rhythm, an alpha rhythm, and a beta rhythm.

21. The real time adaptive system of claim 18, wherein the time domain subcomponents are selected from a group consisting of event-related potentials (ERPs) including N1, P3, and steady state visual evoked response (SSVER).

22. The real time adaptive system of claim 18, wherein the spatial domain subcomponents are selected from a group derived from special transformation of the EEG signal.

23. The real time adaptive system of claim 17, wherein the EEG signal is analyzed by applying one of a group of signal transformation algorithms consisting of a variable epoch frequency decomposition (VEFD), a fast Fourier transform (FFT), and independent component analysis (ICA).

24. The real time adaptive system of claim 17, wherein the EEG signal is analyzed to identify and classify feature clusters from the plurality of signal subcomponents.

25. The real time adaptive system of claim 17, wherein the neurodynamics assessment means create a brain/computer interface feature map (BFM) from a feature cluster identified through one of a group of transformation algorithms consisting of:

discriminant optimization analysis;

wavelet analysis;

distribution function analysis; and fuzzy logic.

26. The real time adaptive system of claim 17, wherein the neurodynamics assessment means perform real-time pattern recognition on the BFM to produce a set of brain/computer interface neural activations (BNAs).

27. The real time adaptive system of claim 17, wherein the cognitive-emotive profile comprises sensorimotor (sense awareness), and psychological (mental awareness) states and their boundary conditions.

28. The real time adaptive system of claim 17, which further comprises feedback signal to control the level of TMS being delivered.

29. The real time adaptive system of claim 17, wherein the signal acquisition means comprises a sensor.

30. The real time adaptive system of claim 17, wherein the processor comprises a central processing unit (CPU).

31. The system of claim 17, wherein the processor comprises a software control program.

32. The real time adaptive system of claim 17, wherein the interactive means integrates a combinatorial TMS stimulation sequence with a combinatorial EEG recording sequence.

33. The real time adaptive system of claim 17, wherein the interactive means effects prolonged changes which include enhancing work performance, rehabilitation for violent behaviors and ameliorating sleep and mood disorders.

34. A method of adaptive intervention of claim 1, wherein the changes in the individual's cognitive-emotive profile include improved memory function or reduction or elimination of symptoms of an illness.

\* \* \* \* \*